(12) United States Patent
Giaever et al.

(10) Patent No.: US 8,227,223 B2
(45) Date of Patent: Jul. 24, 2012

(54) METHOD AND APPARATUS FOR FACILITATING EVALUATING MIGRATION OF CELLS IN VITRO

(75) Inventors: Ivar Giaever, Schenectady, NY (US); Charles R. Keese, Schoharie, NY (US)

(73) Assignee: Applied Biophysics, Inc., Troy, NY (US)

( * ) Notice: Subject to any disclaimer, the term of this patent is extended or adjusted under 35 U.S.C. 154(b) by 633 days.

(21) Appl. No.: 12/360,376

(22) Filed: Jan. 27, 2009

(65) Prior Publication Data
US 2010/0190228 A1 Jul. 29, 2010

(51) Int. Cl.
*C12N 13/00* (2006.01)
(52) U.S. Cl. ............... 435/173.4; 435/173.5; 435/173.6
(58) Field of Classification Search ............... 435/173.1, 435/173.4, 173.5, 173.6, 286.5, 288.4; 204/164, 204/555
See application file for complete search history.

(56) References Cited

U.S. PATENT DOCUMENTS

| | | | |
|---|---|---|---|
| 5,187,096 A | 2/1993 | Giaever et al. | |
| 7,332,313 B2 | 2/2008 | Giaever et al. | |
| 7,399,631 B2 | 7/2008 | Giaever et al. | |
| 2002/0086280 A1 | 7/2002 | Lynes et al. | |
| 2002/0123078 A1 | 9/2002 | Seul et al. | |
| 2004/0152067 A1 | 8/2004 | Wang et al. | |
| 2005/0130119 A1* | 6/2005 | Giaever et al. | 435/4 |
| 2007/0175494 A1 | 8/2007 | Giaever et al. | |
| 2007/0182417 A1 | 8/2007 | Giaever et al. | |

OTHER PUBLICATIONS

Keese et al PNAS, 2004, 101, 1554-1559.*
Lee et al J Biol Chem. Sep. 29, 2006;281(39):29190-200.*
Wang et al LabChip 2008, 8, 872-878.*
Notification Concerning Transmittal of International Preliminary Report on Patentability, International Preliminary Report on Patentability, and Written Opinion of the International Searching Authority, issued for International Application No. PCT/US2010/022169, dated Aug. 11, 2011.
Notification of Transmittal of the International Search Report and the Written Opinion of the International Searching Authority, International Search Report, and Written Opinion, issued for PCT/US2010/022169, dated Oct. 6, 2010.
Wegener et al., "Electric Cell-Substrate Impedance Sensing (ECIS) as a Noninvasive Means to Monitor the Kinetics of Cell Spreading to Artificial Surfaces", Experimental Cell Research, vol. 259, pp. 158-166 (2000).
Keese et al., "Real-Time Impedance Assay to Follow the Invasive Activities of Metastatic Cells in Culture", BioTechniques, vol. 33, No. 4, pp. 842-850 (Oct. 2002).
Giaever et al., "Toxic? Cells Can Tell", Chemtech, American Chemical Society, pp. 116-125 (Feb. 1992).
Keese et al., "Electrical Wound-Healing Assay for Cells in Vitro", PNAS, vol. 101, No. 6, pp. 1554-1559 (Feb. 10, 2004).
Wang et al., "An Automatic and Quantitative On-Chip Cell Migration Assay Using Self-Assembled Monolayers Combined with Real-Time Cellular Impedance Sensing", The Royal Society of Chemistry, Lab Chip, vol. 8, pp. 872-878 (2008).
Hulkower et al., "Quantifying Cell Migration and Invasion", Genetic Engineering & Biotechnology News (Oct. 1, 2008).

* cited by examiner

*Primary Examiner* — Anoop Singh
(74) *Attorney, Agent, or Firm* — Kevin P. Radigan, Esq.; Heslin Rothenberg Farley & Mesiti P.C.

(57) ABSTRACT

Method and apparatus for processing a cell culture are provided. The method includes establishing a cell culture within a holding device having one or more wells, each well holding a cell culture, and including a well substrate with at least one electrode in contact with the cell culture; periodically applying at least one electrical pulse to the at least one electrode to prevent cells from attaching to and achieving confluence over the at least one electrode while allowing cells to attach to and achieve confluence over other portions of the well substrate; and discontinuing the periodically applying of the at least one electrical pulse to the at least one electrode after cells have achieved confluence over the other portions of the well substrate, and thereafter, monitoring the cell culture to monitor migration of cells over the electrode(s) from the other portions of the well substrate.

11 Claims, 10 Drawing Sheets

METHOD AND APPARATUS FOR FACILITATING EVALUATING MIGRATION OF CELLS IN VITRO

TECHNICAL FIELD

This invention relates in general to cell culture processing, and more particularly, to a method and apparatus for electrically preventing cells from attaching to and achieving confluence over one or more electrodes exposed to a cell culture, to thereby facilitate subsequent evaluation of migration of cells over the one or more electrodes.

BACKGROUND OF THE INVENTION

Cell migration is a fundamental property of most mammalian cells involved in the normal development of an organism, as well as in maintenance of the organism, for example, during healing of wounds or in the immune response system to infection. This migration process is also involved in the disease processes such as in the metastasis of cancer cells to establish secondary tumors and in angiogenesis by endothelial cells to support tumor growth. Accordingly, understanding cell migration and control of cell migration are important, and point to control of this behavior as a potential therapeutic target for cancer treatment.

Traditionally, wound healing assays have been employed in evaluating cell migration. Wound healing assays have been carried out in tissue culture for many years to monitor cell behavior, including estimating the migration and proliferative capacities of different cells and of cells, under different conditions.

These assays generally involve first growing cells to form a confluent monolayer. The monolayer is then wounded or disrupted by destroying or displacing a group of cells. Common methods for disrupting the cell monolayer comprise scratching a line (i.e., manually dragging a pointed device) through the layer with any of several different tools such as a needle, razor blade, plastic pipette tip or by removing a small area of cells, e.g., with a spinning circular pad. Additionally, wounding may be carried out using a very small spinning disk to give a more reproducible area to follow. Once a wound is achieved, the wound is then microscopically observed or photographed over time to assess the rate at which the damaged area is filled in by neighboring cells. Unfortunately, the above-noted wounding methods require extensive manipulation of the cultured cells, making these wounding methods expensive and, furthermore, difficult to accurately reproduce, and to verify experimental results.

As noted, after the disruption is accomplished, the area is inspected microscopically at different time intervals as the cells move in and fill the damaged area. This "healing" can take from several hours to over a day depending on the cell type, growing conditions, and the extent of the "wounded" region. The results may be presented by a series of photomicrographs; or in more sophisticated measurements, the microscopic views may be subjected to image processing such that data is expressed in quantitative terms.

An alternative form of measuring cell behavior that replaced the commonly used microscopic observations utilizes electrical sensing. One example is disclosed in U.S. Pat. No. 5,187,096, which is hereby incorporated by reference and referred to herein as the "ECIS™ system". Specifically, the ECIS™ system (Electric Cell-substrate Impedance Sensing) sold by Applied Biophysics, Inc., passively analyzes cell behavior by applying a weak AC current, and measuring voltage changes. The device can be used to monitor various cell behaviors, including morphology changes and cell motions in animal cells that attach and spread out and crawl on the bottom of tissue culture vessels. In the ECIS™ system, cells are grown upon, e.g., a small gold film electrode (e.g., $5 \times 10^{-4}$ cm$^2$) mounted to the bottom of a small well with (in one embodiment) a much larger counter electrode completing the circuit using a standard tissue culture medium as an electrolyte. A weak (e.g., approximately 1 microamp) AC current (usually in the frequency range from 100 to 40,00 Hz) is applied to the electrode. This small current results in a voltage drop across the small, active electrode of only a few millivolts. Voltage drops and currents this small do not affect the health of the cells.

Variations in the measured voltage comprise the measurement. As animal cells attach and spread upon the small, active electrode, they force the current to flow under and between the cells resulting in changes in impedance and hence, in the measured voltage across the electrodes. These changes can be followed and provide a non-invasive means to monitor changes in cell behavior. For example, using the measured voltages, one can infer cell morphology and cell movements, which are important research measurements that form the basis of many biomedical and biological assays.

While the ECIS™ system allows for automated and passive monitoring of cell behavior following a disruption, the traditional requirement of wounding the cell culture still remains.

SUMMARY OF THE INVENTION

Provided herein, in one aspect, is a method of processing a cell culture to evaluate cell migration without requiring wounding or disruption of an established cell monolayer. The method includes: establishing a cell culture within a holding device comprising at least one well for holding the cell culture, the at least one well comprising a well substrate including at least one electrode at least partially exposed to the cell culture; periodically applying at least one electrical pulse to the at least one electrode to prevent cells from attaching to and achieving confluence over the at least one electrode, while allowing cells to attach to and achieve confluence over other portions of the well substrate; and discontinuing the periodically applying of the at least one electrical pulse to the at least one electrode, and thereafter, monitoring the cell culture to monitor migration of cells over the at least one electrode from other portions of the well substrate.

In another aspect, an apparatus for processing a cell culture is provided. The apparatus includes a holding device, a current source, a controller and a monitor. The holding device comprises at least one well for holding a cell culture, and the at least one well includes a well substrate including at least one electrode at least partially exposed to the cell culture. The current source is coupled to the at least one electrode, and the controller is electrically coupled to the current source and to the at least one electrode to control application of current from the current source to the at least one electrode. The controller periodically applies at least one electrical pulse to the at least one electrode to prevent cells from attaching to and achieving confluence over the at least one electrode, while allowing cells to attach to and achieve confluence over other portions of the well substrate, and discontinues the periodically applying of the at least one electrical pulse to the at least one electrode after cells have achieved confluence over the other portions of the well substrate. The monitor monitors migration of cells over the at least one electrode from the other portions of the well substrate after the cells have achieved confluence over the other portions of the well substrate and the periodic application of the at least one electrical pulse to the at least one electrode has been discontinued.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

Generally stated, disclosed herein are a novel electric haptotaxis method and apparatus for facilitating processing of a cell culture, and more particularly, for facilitating monitoring of cell migration over one or more exposed electrodes from other portions of a well substrate. In one implementation, one or more electrical pulses are periodically applied to the exposed electrode(s) of a well containing a cell culture to prevent cells from attaching to and achieving confluence over the exposed electrode(s), while allowing cells to attach to and achieve confluence over other portions of the well substrate. (In one embodiment, the electrical pulses may be applied by a modified ECIS™ system.) Once confluence is achieved (i.e., once a cell monolayer is established over the other portions of the well substrate), the periodic application of electrical pulses to the exposed electrode(s) is discontinued, and migration of cells over the exposed electrode(s) from the other portions of the well substrate is monitored. Various approaches may be used in monitoring migration of the cells. For example, microscopic observation or a series of photomicrographs may be obtained and evaluated. Alternatively, the ECIS™ system approach may be employed in characterizing migration of cells over the exposed electrode.

Figure 1:
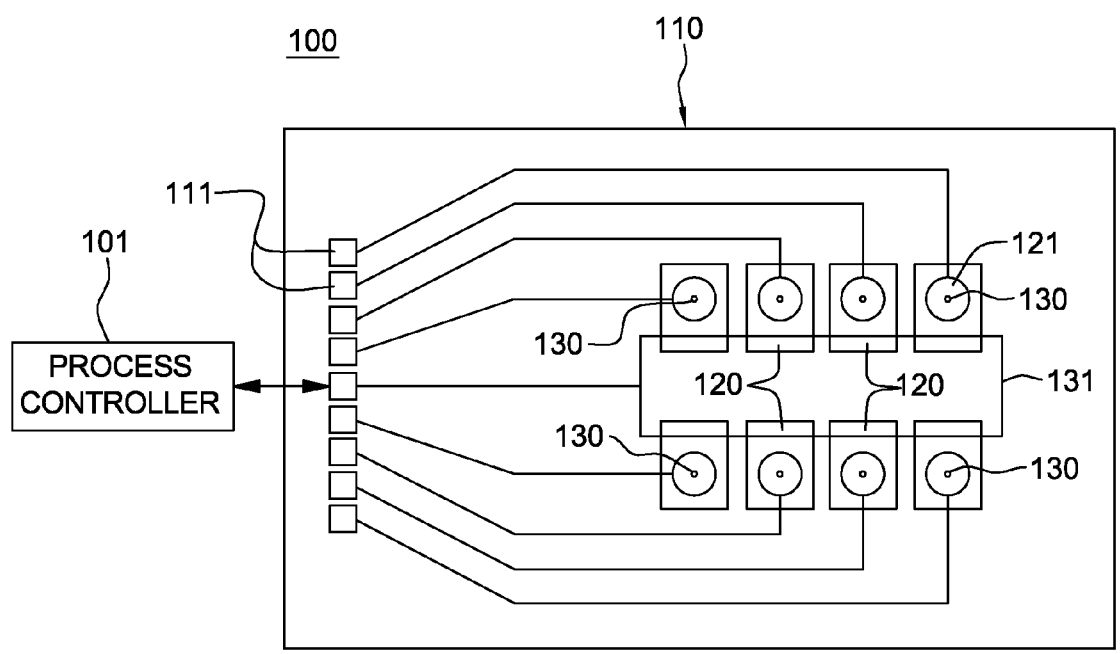
FIG. 1 depicts one embodiment of a holding device and a process controller of an apparatus for processing a cell culture, in accordance with an aspect of the present invention.

FIG. 1 depicts one embodiment of a partial apparatus, generally denoted 100, in accordance with an aspect of the present invention. This apparatus includes a holding device 110 comprising an array of wells 120, each of which includes a respective pair of electrodes 130, 131. In the embodiment depicted, electrode 130 is assumed to be a small portion of a larger supporting electrode 121, with only the small portion of supporting electrode 121 being exposed to the cell culture within the well. For example, an insulating film could be disposed over the lower surface (or well substrate) of each well, with an appropriately sized opening provided in the insulating film to expose electrode 130. In the configuration depicted, electrode 130 is a smaller electrode than electrode 131, and is referred to herein as the "active electrode", with electrode 131 being referred to as the "counter electrode".

The pairs of electrodes are electrically controlled by a process controller 101 to, for example, electrically restrict attachment of cells to exposed electrodes 130, and thereafter, to monitor cell migration across the exposed electrodes. Exposed electrodes 130 are connected to electrical connectors 111 by respective electrical pathways. Counter electrodes 131 are situated proximate each exposed electrode 130, as explained further below. Current passes from electrical connectors 111, along the electrical pathways, to the exposed electrodes 130, and then through the cell culture and/or electrically conductive medium, to the counter electrodes 131 and hence back to electrical connectors 111. In this embodiment, process controller 101 is assumed to control the application and signal strength of current applied to the electrical connectors, as explained further below, and individual cell cultures are assumed to have been selectively placed into the depicted experimental wells 120.

Process controller 101 may be implemented as a dedicated controller, or as a general purpose computer configured with control functionality such as described herein. Further, process controller 101 may include one or more user interfaces to allow a user to control or tailor control of cell culture processing, in accordance with an aspect of the present invention. This user interface may include a display, keyboard, mouse, voice recognition system, etc.

Figure 2:
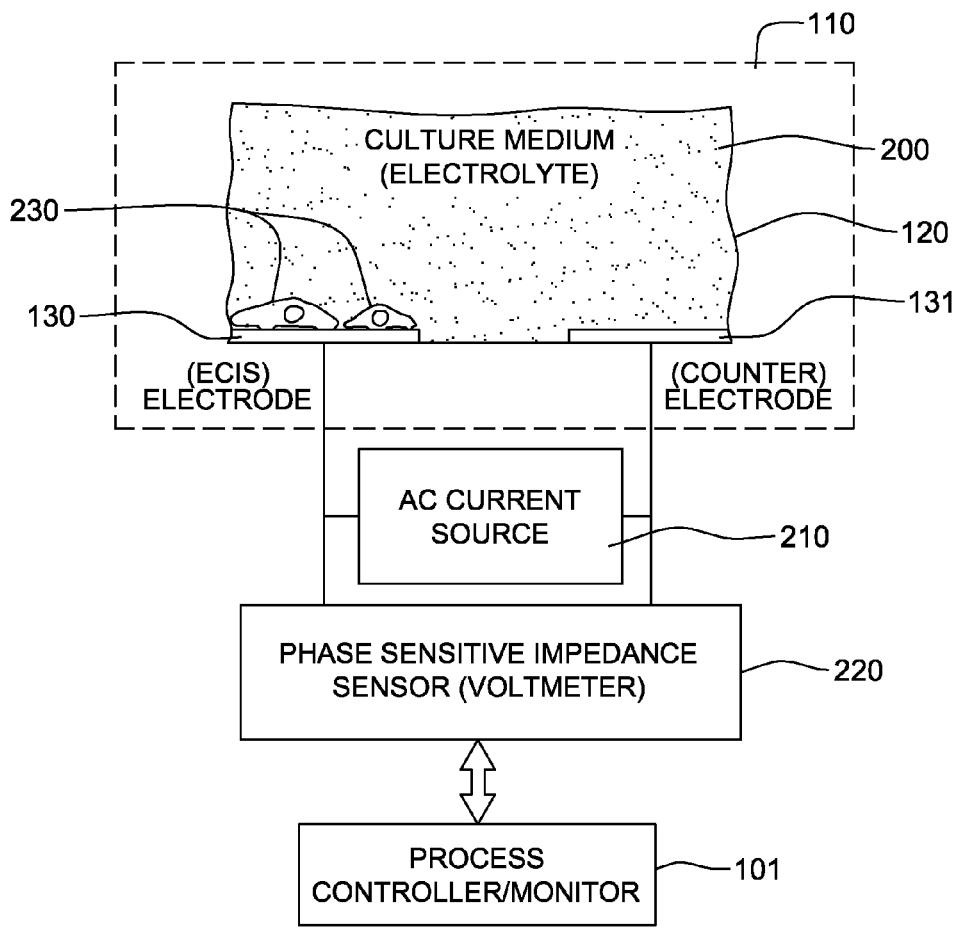
FIG. 2 depicts further details an apparatus for processing a cell culture, in accordance with an aspect of the present invention.

FIG. 2 depicts further details of an apparatus for processing a cell culture, in accordance with an aspect of the present invention. In this embodiment, the apparatus includes one or more wells 120 (partially depicted) within a holding device 110. Well(s) 120 again includes a first electrode 130 and a second electrode 131, which in one example, are respectively an ECIS electrode of an ECIS™ system and a counter electrode. Well 120 is shown to include a culture medium 200, which may be an electrolyte, and cells 230, which are illustrated on electrode 130. Presence of cells 230 on electrode 130 may be monitored by monitoring impedance between electrode 130 and electrode 131. In electric cell-substrate impedance sensing (ECIS), cells are cultured and detected on the electrodes (e.g., small gold film electrodes, generally 250 micrometers in diameter or less). As used herein, "electrode" refers to an exposed portion of an underlying electrode which is in communication with the culture medium. As explained further below, each such electrode may comprise an opening in an insulative layer to the larger supporting electrode (e.g., see FIG. 1).

An AC current source 210 is electrically connected between electrode 130 and electrode 131 and is, in one embodiment, controlled by a process controller/monitor 101. During ECIS™ monitoring, a weak AC signal is applied between, in one embodiment, the smaller measuring electrode 130 and the larger, counter electrode 131. The tissue culture medium 200 again serves as the electrolyte. Measurements are managed by process controller/monitor 101, which as noted above, may comprise a computer-implemented controller. Process controller/monitor 101 monitors the measured impedance obtained via, for example, a voltmeter 220. Note that an ECIS™ system can employ one of two different forms of voltage measurement. A first version utilizes a voltmeter which reports simple impedance in ohms, and does not have a phase-sensitive detector. A more advanced ECIS™ system monitors both voltage and phase, and reports impedance (that is, resistance and capacitance), treating the electrodes with the medium and cells as a series RC circuit. With this information, certain data can be modeled and reports generated related to cell properties. For example, capacitance can be used to detect how much area of the electrode is exposed, while resistance and capacitance together provide additional information about real cell parameters, and how tight the cells are joined together. The concepts presented herein may be employed with either impedance measurement approach.

Process controller/monitor 101 thus controls the applied AC signal, monitors the measured impedance, and switches the measurement to different electrodes in the holding device in the course of an experiment. As cells anchor (or attach) and spread on the active electrode(s), their insulating plasma membranes constrain the electrical current and force it to flow beneath and between the cells. This convoluted current path causes large changes in the measured impedance. In addition, once confluence is achieved, small fluctuations in impedance may be observed because the live cells continuously alter their morphology. These impedance changes and fluctuations can be analyzed to indirectly report real-time changes in cell morphology.

Figure 3:
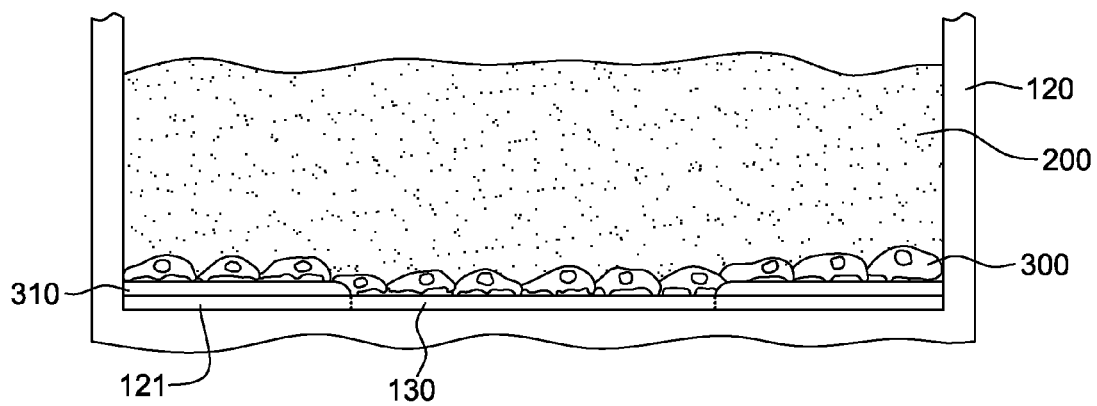
FIG. 3 depicts a partial embodiment of an apparatus for processing a cell culture, wherein a well of a holding device is illustrated containing a cell culture, and with the well substrate including at least one electrode in contact with the cell culture and a cell monolayer formed over the well substrate, in accordance with an aspect of the present invention.

By way of further example, FIG. 3 depicts (not to scale) one embodiment of a well 120 having a cell culture medium 200 disposed therein with a cell monolayer 300 formed across the well substrate 310. As illustrated, the well substrate includes an exposed electrode 130 across which the cell monolayer 300 extends. In this embodiment, exposed electrode 130 is a portion of a larger, supporting electrode 121 disposed beneath the surrounding portions of well substrate 310. As used herein, the phrase "well substrate" refers to the lower surface of well 120 and may include one or more exposed electrodes or exposed portions of electrodes in communication with the cell culture medium 200, for example, across a protein layer such as described below. In one implementation, well substrate 310 is an insulating layer isolating underlying electrode 121 from the cell culture medium, with only one or more smaller electrodes 130 exposed. As one detailed example, exposed electrode 130 is approximately 250 micrometers, or less, in diameter. This size restricts the maximum cell populations that can be observed using a single electrode to about 100 cells, but it should be noted that the activities of even an isolated cell could be readily measured using the above-described ECIS™ system approach.

FIGS. 4A-4D depict various alternate electrode pair configurations which may be employed in the well(s) of an apparatus in accordance with an aspect of the present invention.

Figure 4A:
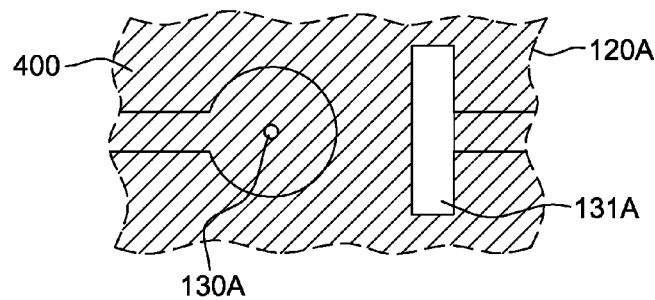
FIGS. 4A-4D depict various embodiments of electrode pair configurations which may be employed in the well substrate(s) of the well(s) of the holding device of an apparatus, in accordance with an aspect of the present invention.

In FIG. 4A, a single small, exposed electrode 130A within well 120A is in communication with the cell culture medium therein and is defined by an opening in an insulating film 400 which extends over the underlying electrodes. A larger, counter electrode 131A is shown in relatively close spaced relation to electrode 130A to complete the electrical circuit. As noted above, in one example, small exposed electrode 130A is the active electrode and is approximately 250 micrometers in diameter, or less (in one example). More generally, the concepts presented herein may be employed with an active circular electrode in the range of 50 micrometers to 1 or 2 mm.

Figure 4B:
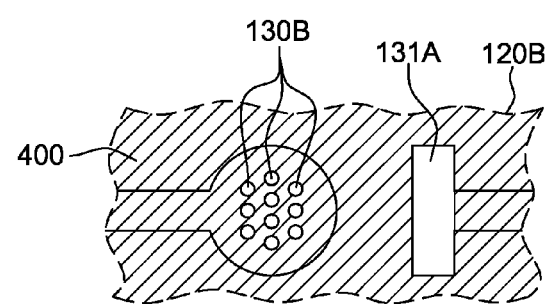

In FIG. 4B, multiple small, exposed electrodes 130B are formed by multiple openings in insulating film 400 to the underlining support electrode, each of which may be an approximately 250 micrometer diameter (or less) electrode. Again, a counter electrode 131A is disposed in opposing relation to the multiple exposed electrodes 130B of well 120B.

Figure 4C:
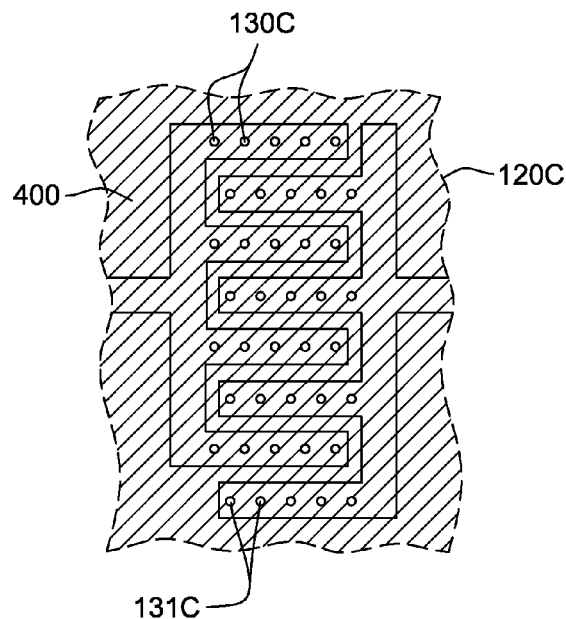

In FIG. 4C, a portion of a well 120C is illustrated wherein the underlying electrode structures are interdigitated, with each electrode structure comprising, in this example, 20 exposed electrodes 130C, 131C. Again, each exposed electrode 130C, 131C might comprise, for example, an approximately 250 micrometer diameter opening through insulating film 400. In an alternate implementation, the concepts disclosed herein could be employed with exposed interdigitated electrodes in the well substrate.

Figure 4D:
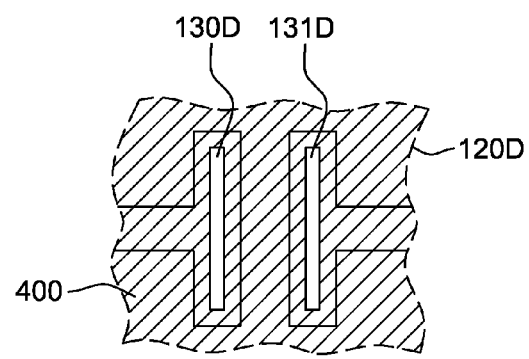

In FIG. 4D, a portion of a well 120D is illustrated wherein the underlying electrode structures are in opposing relation and comprise rectangular (or line) exposed electrodes 130D, 131D defined through insulating film 400, as illustrated.

Those skilled in the art should note that various other electrode pairing configurations may also be employed. For example, the single and multiple electrodes of FIGS. 4A & 4B could be employed with a different counter electrode configuration. Further, any number of exposed electrodes could be presented in one or both electrode structures of the pair of electrode structures in any well of the holding device. A variety of different well arrays may be employed within a holding device, with 8 wells and 96 wells being two common examples. Within the holding device, the electrode pairings may be uniform among the wells, or may be configured and/or sized differently among the wells. In certain embodiments, the active electrode(s) is preferably sufficiently small in size to be able to detect the presence of the cell monolayer over the exposed electrode(s) as a change in impedance. This limitation is beneficial for a process monitor comprising the ECIS™ system. Size of the active electrode(s) is not as critical if a different monitoring approach is to be employed.

Still further, the shape of the exposed electrodes may vary, and both electrode structures may include more than one exposed electrode, as illustrated, for example, in FIG. 4C. In FIG. 4C, the 40 active electrodes, 20 in each electrode structure, are essentially arranged in parallel, making it possible to look at a considerably larger number of cells in a confluence cell layer. (Note that in FIG. 2, two cells (not drawn to scale) are shown attached to the small, active electrode. However, in most experiments, a confluent layer of cells covers all electrodes in addition to the intervening well substrate surfaces, which may be covered in one example by an insulating film (see FIGS. 4A-4D)). Note also that with a small applied AC current density (<2 mA/cm$^2$), the resulting voltage drop (of a few millivolts) has no detectable affects on the cells attached to the electrodes, and thus the ECIS™ system measurement discussed herein is non-invasive.

Figure 5:
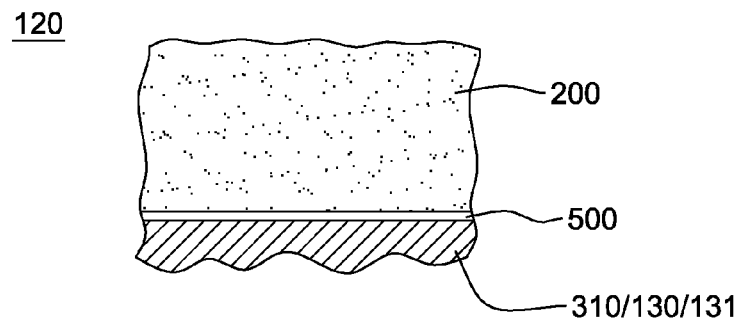
FIG. 5 is a partial elevational depiction of a well comprising a cell culture with a protein layer formed over the depicted portion of the well substrate, in accordance with an aspect of the present invention.

As background to the inventive process disclosed herein, FIG. 5 depicts a partial cross-section of a well 120, wherein the cell culture includes a culture medium 200 and an absorbed protein coating (or layer) 500 conformally established over the insulating film 310, exposed electrode 130 or counter electrode 131. This protein layer 500 facilitates cell growth. Depending upon the test setup, different protein layers may be established and analyzed for their effect on cell migration.

Figure 6:
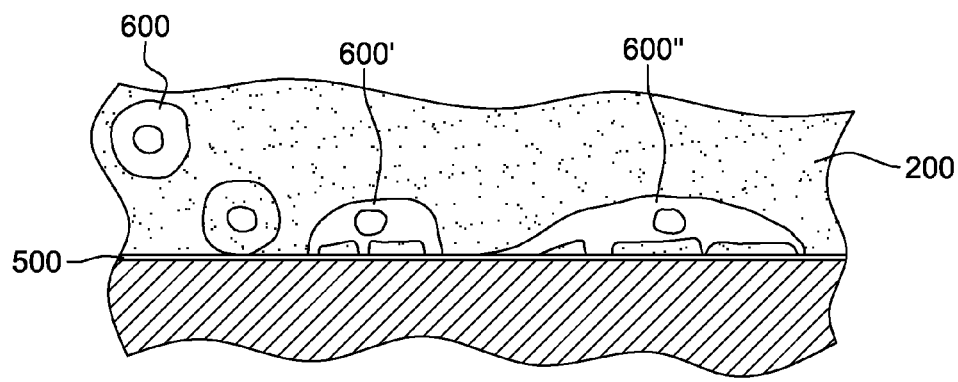
FIG. 6 is a partial elevational view of a well comprising a cell culture and illustrating attachment of a cell to the well substrate across the protein layer, in accordance with an aspect of the present invention.

FIG. 6 illustrates a cell 600 in a culture medium 200 of a well having a protein layer 500 disposed over the well substrate. As illustrated, the cell physically contacts (or lands) on protein layer 500 and proceeds to attach to protein layer 500, which results in a reconfigured cell 600'. The reconfigured cell then migrates, resulting in a further elongation of the cell 600".

Figure 7:
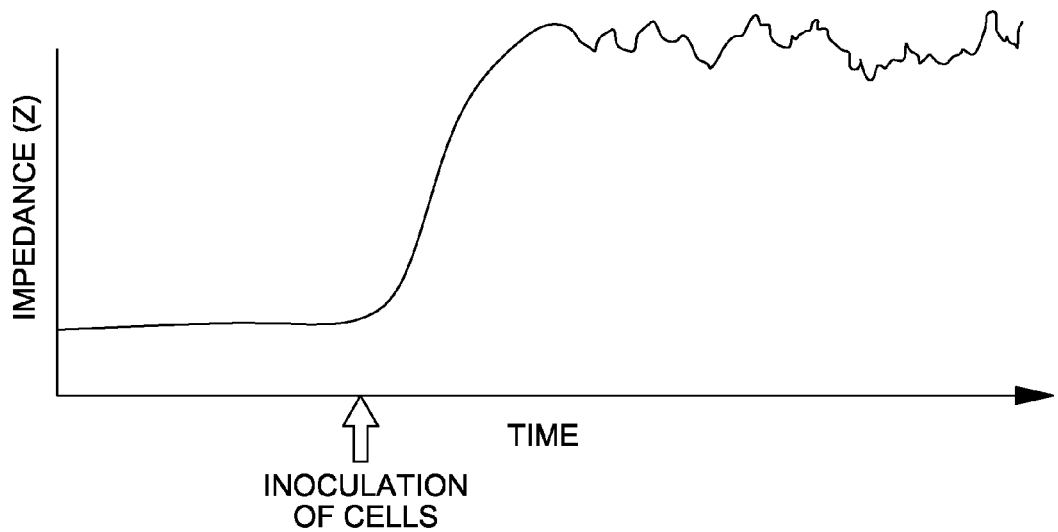
FIG. 7 graphically depicts impedance between electrodes of a well of the apparatus of FIG. 2 with inoculation, attachment and growth of cells over the exposed electrode(s) as confluence over the well substrate (including the exposed electrode) is achieved.

As further background, an ECIS™ system and monitoring approach may be employed in a wide variety of applications. FIG. 7 illustrates a conventional plot of impedance of a cell line as a cell monolayer is formed over a well substrate as a function of time. Depending on the cell line at issue, achieving confluence over the well substrate may take from several to many hours or days. Inoculation of cells into the well is assumed to occur in the example of FIG. 7 at the time (or shortly preceding) the increase in impedance noted in the graph. Once confluence is achieved, the impedance signal shows fluctuations that are related to cell movements within the confluent monolayer. Using a similar assay, but absorbing different protein layers upon the electrodes before cell inoculation, results in behavioral changes of cell interactions with the extra-cellular matrix proteins, which may be studied.

The ECIS™ system, and the cell culture processing and apparatus described hereinbelow, may be employed in a variety of applications. These applications include: measurement of extravasation endothelial cell layers; G-protein coupled receptor signal transduction; endothelial cell barrier function; in vitro toxicology; cytopathic effects of viral infections; monitoring the affects of electroporation; and chemotaxis measurements.

For example, ECIS™ has been documented to monitor extravasation of endothelial cell monolayers when exposed to suspensions of metastatic cells. In this work, ECIS™ electrodes were first covered with confluent layers of human endothelial cells (HUVEC). These established layers were subsequently exposed to suspension of metastatic cells and the impedance measured. Using murine prostatic carcinoma cell lines, a strong and reproducible drop in impedance was measured in response to the cell challenge. Furthermore, the rate and extent of this reduction was observed to be dependent upon the in vitro metastatic potential of the cancer cells. Similar results were obtained when confluent HUVEC endothelial cell layers were challenged with four different human prostatic carcinoma cell lines.

Studies have also supported the use of ECIS™ as a whole cell biocensor to monitor signal transduction cascades. Working with CHO cells over expressing the muscarinic receptor, it has been demonstrated that there is a doubling of impedance at 4000 Hz upon binding of the agonist carbachol. Furthermore, this response has the accepted EC50 value and can be inhibited by the antagonist pirenzepine. Similar results have been reported with other G-protein coupled receptors. For example, the impedance response of endothelial cells (BAEC) following the binding of the agonist isoproterenol (ISO) to the β-adrenergic receptor results in a readily measured increase in the impedance of the cell layer. These impedance changes in response to the addition of a ligand suggest that the signal transduction cascade eventually impinges upon the cells cytoskeleton, changing the cell morphology, the path of electrical current flow, and in turn, the impedance.

Still further, endothelial cell barrier function using ECIS™ have been demonstrated. In this work, the drop in impedance upon exposure of confluent bovine aortic endothelial cells to thrombin was monitored and the data was demonstrated to replicate more traditional barrier function measurements. Since that time, a growing number of laboratories have been making permeability measurements of endothelial cell layers using ECIS™ measurements since it reproducibly reports changes in this property in real-time, without the need for labeled molecules.

As noted above, cell migration is a fundamental property to be measured and characterized, both for development of a normal organism, for example, during the healing of wounds or in the immune response system to infection, as well as possibly controlling cancer cells.

An ECIS™ system may be used to measure rates of cell migration using, for example, a traditional scrape wound-healing assay, where a confluent cell layer is scraped to remove a narrow strip of cells, and the healthy cells on the edge of the wound migrate inward to fill the void. By making optical measurements of this activity, one determines the rate of cell migration. An ECIS™-based version of this assay uses high electric fields to wound the cell monolayer by killing cells on an active electrode, and following this, to employ the typical non-invasive ECIS™ measurement to monitoring the healing/migration process. FIGS. 8A-8D illustrate this wounding process.

Figure 8A:
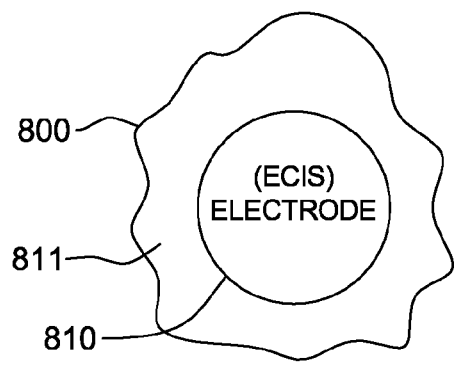
FIG. 8A-8D depict one embodiment of cell monolayer growth over an active electrode (such as an active electrode of an ECIS™ system), followed by wounding of the cell monolayer over the electrode and monitoring of cell migration back over the electrode.
Figure 8B:
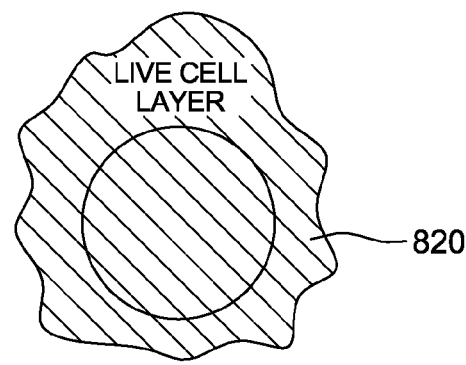
Figure 8C:
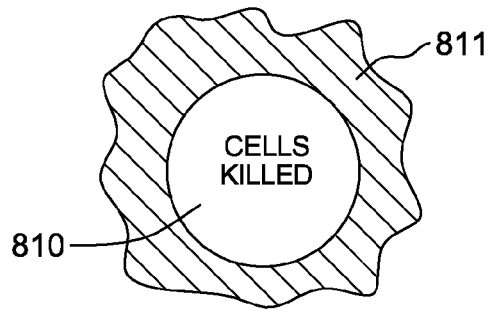
Figure 8D:
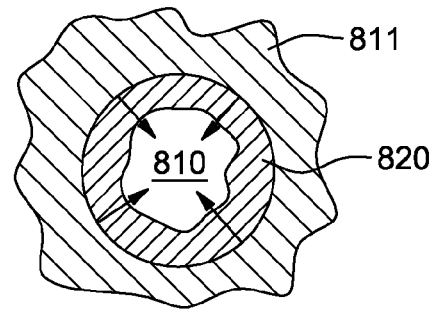

In FIG. 8A, a portion of a well 800 is illustrated, wherein an insulating film 811 of a well substrate surrounds an electrode 810, which in this example is labeled an ECIS™ (or active) electrode. In FIG. 8B, a live cell monolayer 820 is shown established over the well substrate, including the electrode. In FIG. 8C, a high electric field has been applied to the electrode to kill the live cells over electrode 810, leaving live cells only over the surrounding well substrate 811. In FIG. 8D, live cells 820 are shown migrating inward from the monolayer over well substrate 811 to heal the wound. This wounding approach is illustrated in further detail in FIGS. 9 & 10, and described in detail in commonly assigned U.S. Pat. No. 7,332,313, which is hereby incorporated herein by reference in its entirety.

Figure 9:
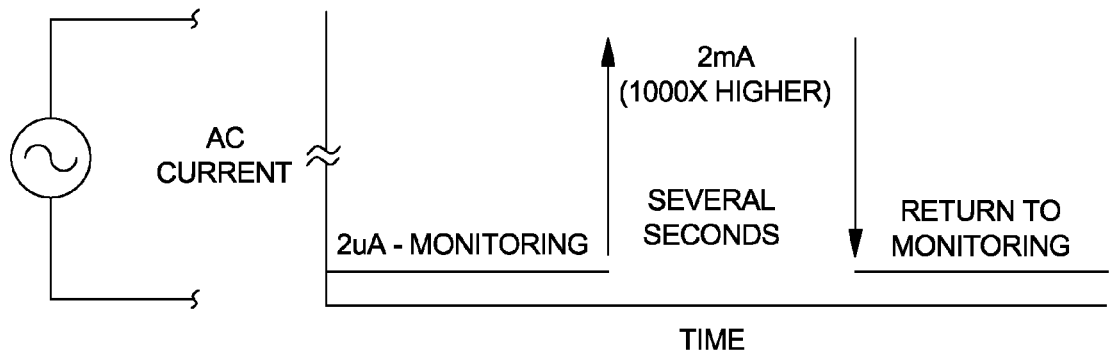
FIG. 9 is a graph of the applied signals in the electrical wounding approach of FIGS. 8A-8D, wherein a high power AC electrical signal is applied between the electrodes of the well to inflict wounding and killing of the cells over the active electrode after the cell monolayer has been formed, as illustrated in FIG. 8B.

FIG. 9 illustrates an AC current signal, which has a small signal value of, for example, approximately two micro-amperes during a monitoring time interval, and a higher current value, for example, two milliamperes during a wounding (i.e., killing) time interval, lasting several seconds, before returning to the monitoring current value.

Figure 10:
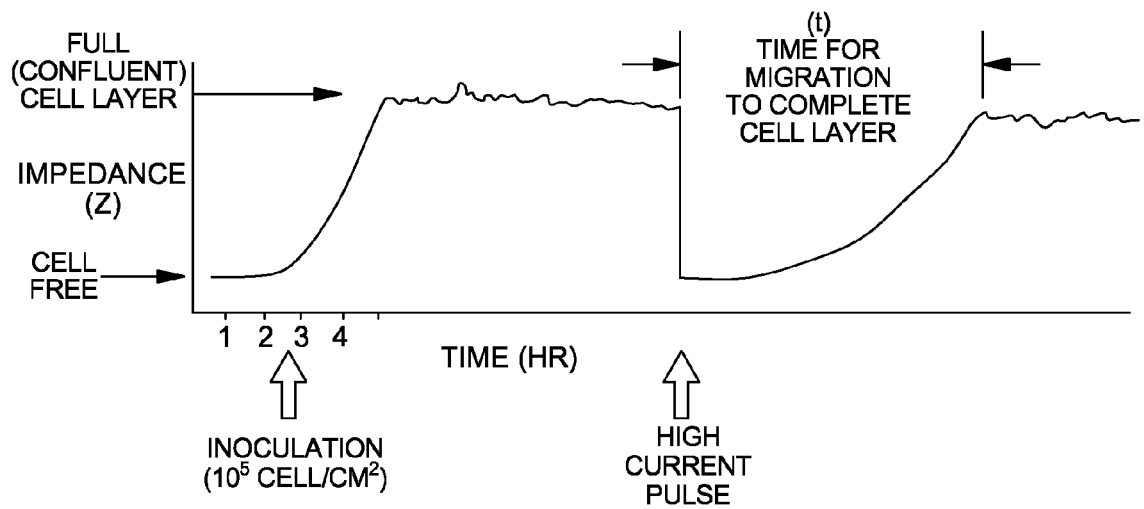
FIG. 10 graphically illustrates measured impedance changes using an ECIS™ system to monitor presence of the cell monolayer over the ECIS™ electrode as the monolayer is established, wounded and then re-grown, as shown in FIGS. 8A-8D.

FIG. 10 illustrates impedance of a cell monolayer showing a wounding (after inoculation of cells and establishment of a full cell monolayer), which is followed by a gradual increase in impedance over a time (t) equivalent to the time required for the cells to migrate completely over the electrode, displacing dead cells on the electrode. As shown, by applying the high current signal to the electrode, a full wound is achieved, dropping the resistive portion of the impedance to an open electrode value. Additional exposure to the elevated field does not alter these results. In this manner, a precise wound can be achieved with only rudimentary control of the time that the elevated field is applied. If one assumes a constant rate of radial velocity, then the time to return to confluent impedance can be used in calculating the migration rate of the cells. This assay, being electrical in nature, is quantitative and has proven to be highly reproducible, capable of working with most animal cells in a culture and easily automated.

Although this wounding approach works well with many cell types, certain cell lines cannot be measured in this manner. A problem arises when, upon application of the high electric field, the dead cells remain firmly attached to the electrode. In this case, the live cells are unable to move inward and displace the killed cells. With migration even partially blocked, the measurement cannot be used in a reliable manner. Additionally, by first allowing live cells to attach to and form a monolayer over the electrode before wounding the cells, the conformal protein layer over the electrode may be modified by the live cells during the time that the cells are attached to the electrode. It is known that cells can synthesize and excrete proteins, polysaccharides, etc., to modify their environment in vivo. In tissue culture, cells can deposit these extracellular materials and in this manner modify the surface on which they are growing. Examples of such extracellular matrix proteins include collagen, fibronectin and elastin. This modification of the protein layer also affects the reliability of the experiment.

As noted briefly above, the surfaces upon which cells grow in a tissue culture are typically coated with macro-molecules (usually proteins) that spontaneously absorb to the solid interface. It is possible to define these protein coats by first exposing the surface to a solution of the protein of interest (for example, collagen). If no specific protein is applied in this manner, then the surface will typically pick up proteins from the tissue culture medium that sustains the cells in culture.

When a tissue culture well is inoculated with mammalian and other animal cells, the cells are initially in a spherical shape. Being slightly more dense than the medium in which they are grown, these cells will settle on the protein-coated floor of the well (i.e., the well substrate). There, the cells begin to actively adhere (i.e., attach) to the substrate and then change their morphology and flatten (or spread) upon the surface as described above in relation to FIG. 6. This cell attachment and spreading generally requires a few hours, depending upon the cell line. The cells will then go through rounds of cell division (approximately one division per day), until the surface is covered with a cell monolayer (i.e., confluent). This confluent state can also be achieved immediately following cell spreading if a sufficiently high number of cells is added to the well (approximately 100,000 cells per square centimeter).

In accordance with an aspect of the present invention, electro-restriction (or electric haptoaxis) is employed to prevent cell attachment and spreading of live cells over the electrode(s) until the cell monolayer is established over the balance of the well substrate. This electro-restriction is achieved by periodically applying one or more electrical pulses, preferably of a high electric field, to the electrode(s) in the well(s) of the holding device. Note that, depending on the electrode configuration, this electro-restriction can be achieved for the active electrode(s) only, or both the active electrode(s) and counter electrode(s). In the example of FIGS. 4A & 4B, where the counter electrode is distinctly larger than the active electrode(s), then the voltage drop across the counter electrode is much smaller than the active electrode, and cells will attach and spread on the counter electrode surface, even in the presence of the high current pulses. However, if the counter electrode(s) is another small electrode, such as depicted in FIG. 4D, or a collection of small electrodes, as in the case of FIG. 4C, then cell layer formation will be restricted over both sets of electrodes, that is, the cells will be unable to attach and spread on the electrodes during the pulsing of a relatively high current signal through the electrodes.

Figure 11:
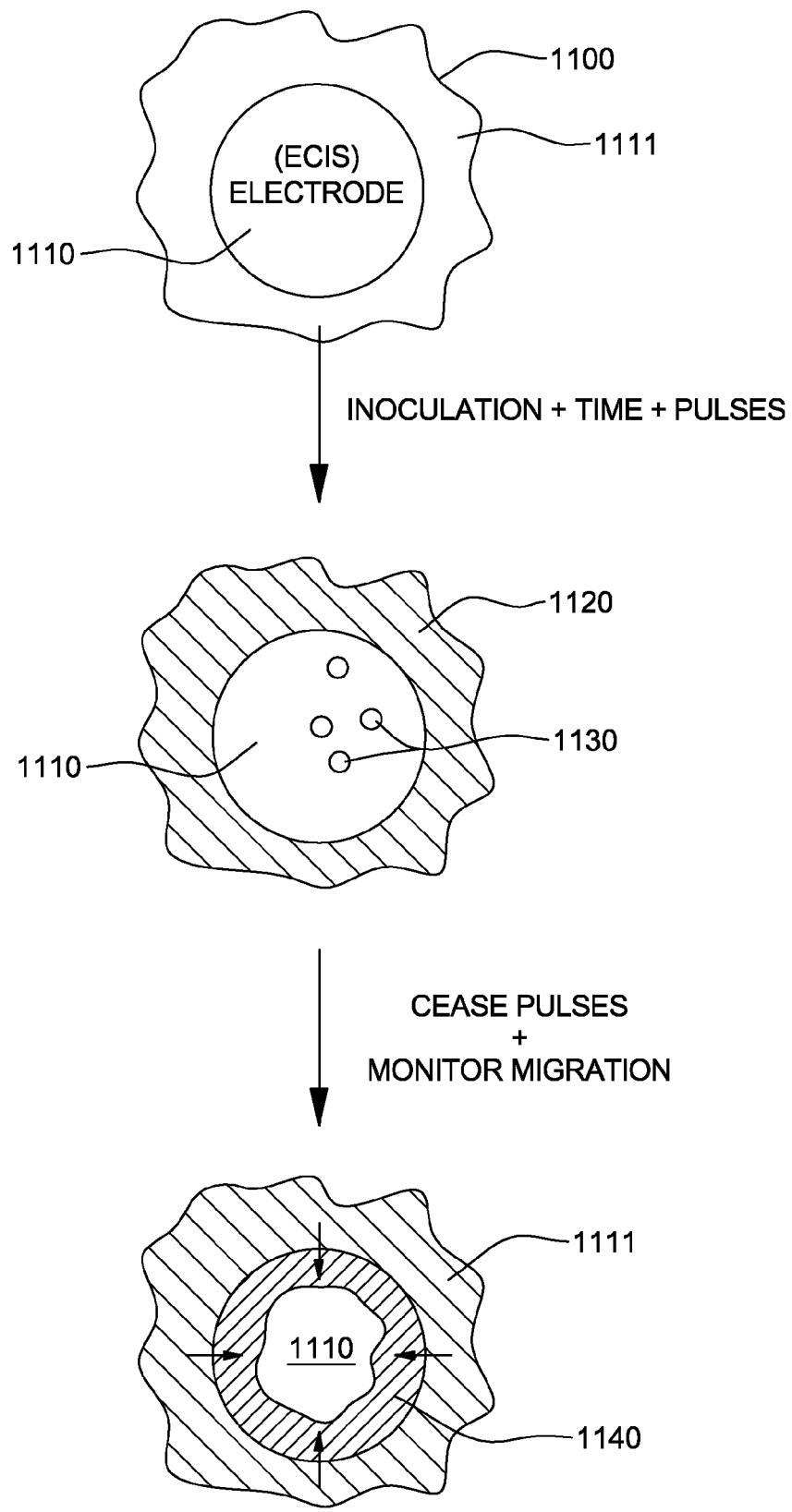
FIG. 11 is a representation of a process for selectively allowing cells to achieve confluence only over portions of the well substrate other than the exposed electrode(s), followed by migration of cells over the exposed electrode, in accordance with an aspect of the present invention.

For example, FIG. 11 partially depicts a well 1100 wherein an electrode 1110, such as an ECIS™ electrode (or active electrode of an ECIS™ system), is exposed in a well substrate 1111. Subsequent to cell inoculation, one or more electrical pulses are periodically applied to the electrode to prevent cells 1130 from attaching to and achieving confluence over the electrode, while allowing cells to attach to and achieve confluence over the other portions of the well substrate 1120. At some point after confluence is achieved over the balance of the well substrate, the periodic application of electrical pulses to the electrode is discontinued, and migration of live cells 1140 over electrode 1110 from the monolayer over well substrate 1111 is monitored. This monitoring could be via, for example, a microscope, or alternatively, employing an ECIS™ system such as described hereinabove.

Figure 12A:
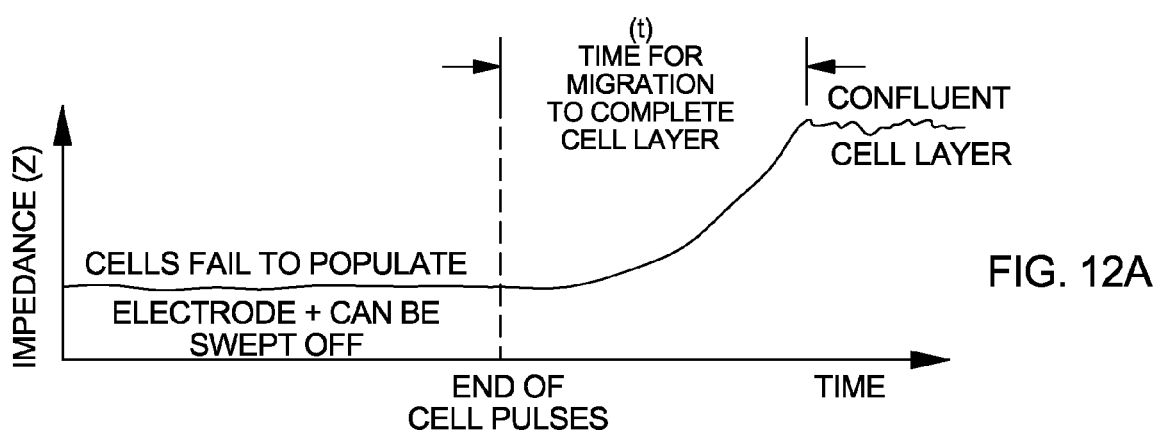
FIGS. 12A & 12B graphically illustrate ECIS™ impedance measurements during and after the periodic application of one or more electrical pulses to an electrode(s) of a well to prevent cells from attaching to and achieving confluence over the electrode, and after discontinuing the periodic applying of the one or more electrical pulses, the monitoring of cell migration over the electrode from other portions of the well substrate, in accordance with an aspect of the present invention.
Figure 12B:
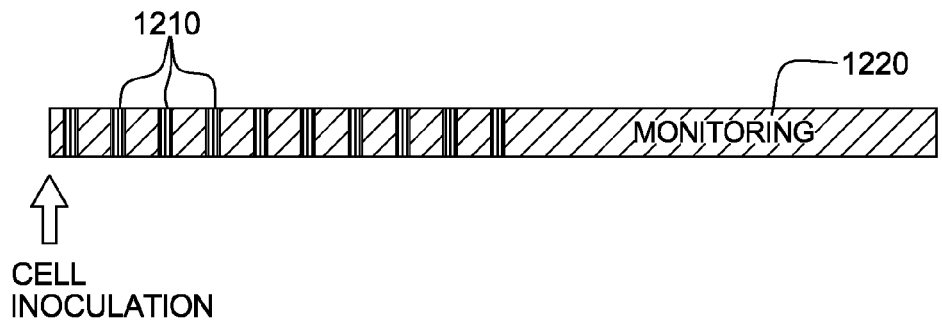

FIGS. 12A & 12B depict the impedance measured across the well of FIG. 11 using an ECIS™ system. In FIG. 12A, the impedance remains low, notwithstanding cell inoculation since cells are unable to attach to and achieve confluence over the electrode due to the periodic application of one or more relatively high current electrical pulses. At some later point, preferably (but not necessarily) after the cells have achieved confluence over the surrounding well substrate, the periodic application of the one or more electrical pulses is discontinued, allowing the migration of cells inward from the surrounding monolayer until a confluent cell layer is achieved over the electrode as well.

In FIG. 12B, an electric restrictive interval is shown wherein one or more electrical pulses 1210 are periodically applied to the electrode, after which the current value through the electrode decreases to a monitoring level 1220 for ECIS™ monitoring, as described above. As one detailed example, each 250 micrometer diameter electrode may be pulsed with a current on the order of 0.5-10 milliamperes (or higher) at 1-100 kHz every few minutes. The frequency of the pulses must not be too low to prevent damage to the electrodes. In one specific implementation, electrical pulses with an approximately 40 kHz frequency and a current in the milliampere range are applied to the electrodes during the electro-restriction phase of the process. This high electric field pulse applied comprises, in one example, three to five cycles of current on (approximately 200 m/sec. on) and off (approximately 200 m/sec. off), with the pulse sequence repeated every few minutes. In an alternate embodiment, the sequence may comprise more or fewer pulses, including a single AC pulse which is periodically repeated during the several hour long period when the inoculated cells are expected to attach and spread on the well substrate. The effect is that cells remain rounded over the electrodes carrying the high field pulse sequence, whereas cells in other locations on the well substrate form a complete monolayer. During this time, the rounded cells may easily be removed or swept from the electrode by a gentle stream of medium, or slide off the electrodes if the wells are tipped slightly.

Upon turning off the high field pulsing sequence, and switching to only ECIS™ monitoring mode (that is the low current monitoring mode) migration of cells into the open electrode areas may be detected, and the migration rate readily calculated.

Figure 13:
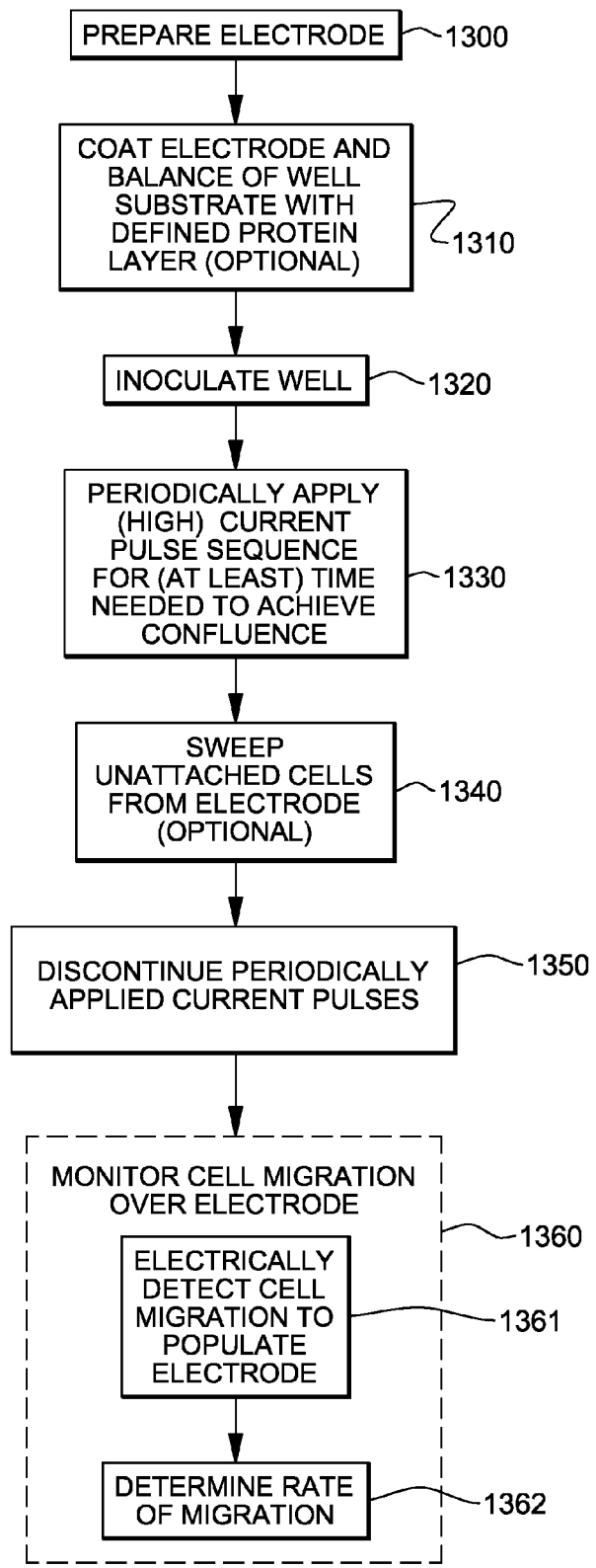
FIG. 13 is a flowchart of one embodiment of a process for temporarily preventing and then monitoring migration of cells over an electrode of a well, in accordance with an aspect of the present invention.

In FIG. 13, a process overview is provided. This process embodiment includes preparing the electrode(s), which may include cleaning the electrode, if desired. Cleaning (or preparing) the electrode(s) may be helpful, particularly if the electrode(s) has been in storage for a period of time prior to use. A final step in manufacturing an electrode(s) such as described herein is an oxygen plasma etch that cleans the surface of the electrode, which in one implementation, is a gold surface. Over time, small molecules may absorb to the electrode surface, reducing the measured capacitance of the open electrode. These small molecules can desorb in the culture medium, causing unwanted drifts in the electrode impedance.

One solution to stabilizing the electrode involves treating each well with an approximately 200 microliters of a 10 mM solution of cysteine in water (which is commercially available as an ECIS™ electrode-stabilizing solution). After exposing the wells to the solution for approximately 10 minutes at room temperature, the solution can be aspirated from the wells, followed by several rinses of sterile, distilled water. The wells can then be coated with proteins or have the culture medium added for immediate use. Note that the —SH residue of the cysteine will form covalent linkages with the gold electrode surface, and the organic layer coating the gold will remain in place and maintain the electrode capacitance to that of a new array.

Another approach to stabilizing the electrode(s) is described in commonly assigned, U.S. patent application Ser. No. 11/670,464, filed Feb. 2, 2007, entitled "Electrode Cleaning Using Electrical Pulse", which published on Aug. 2, 2007, as U.S. Patent Publication No. 2007/0175494 A1, the entirety of which is hereby incorporated herein by reference. Briefly summarized, this commonly assigned application describes an electrode cleaning approach using electrical pulses. For example, an electrical pulse can be employed to cause a voltage drop of approximately 0.01 volts to approximately 10 volts across the electrode. This voltage drop results in cleaning of the electrode, without apparently disrupting the absorbed protein coating.

Continuing with FIG. 13, the electrode is next optionally coated, as well as the balance of the well substrate, with a defined protein layer 1310. Cells are inoculated into the culture medium of the well 1320, and a high current pulse sequence is periodically applied for at least the time required to achieve confluence of live cells over the well substrate, that is, over the other portions of the well substrate from the electrodes having the periodically applied current pulse sequence. Any unattached, lone cells may be swept or removed from the electrode(s) 1340, after which the periodically applied current pulses (or pulse sequence) are discontinued 1350 and cell migration over the electrode is monitored 1360. In the ECIS™ monitoring approach, a low current signal is applied to the electrodes to electrically detect cell migration and population of the monolayer over the electrode 1361, from which the rate of migration can be readily determined 1362.

Figure 14A:
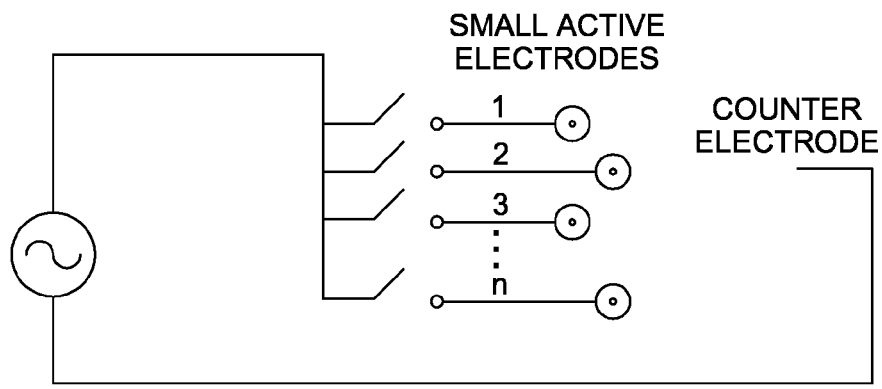
FIG. 14A is a schematic of one embodiment of an apparatus for electrically restricting cell attachment to electrodes of a plurality of wells of a holding device, in accordance with an aspect of the present invention.
Figure 14B:
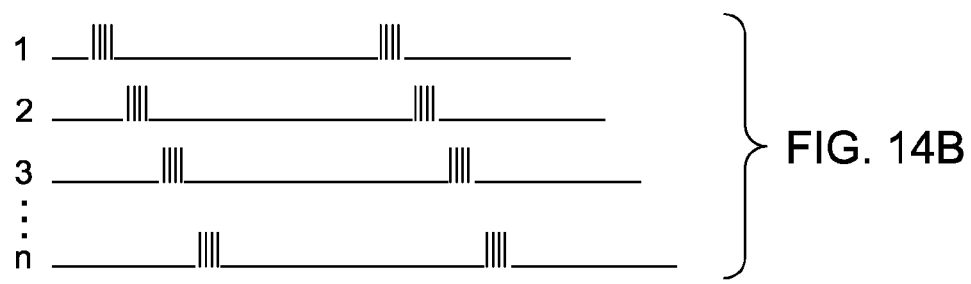
FIG. 14B depicts one electric-based control implementation wherein a signal pattern comprising a sequence of electrical pulses is sequentially, periodically applied to the electrodes of the wells of the holding device of FIG. 14A, in accordance with an aspect of the present invention.
Figure 14C:
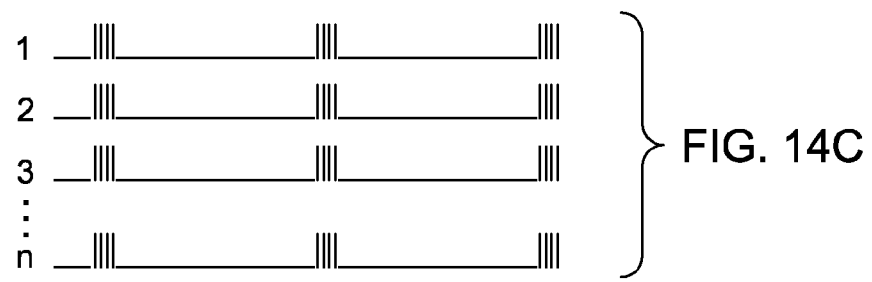
FIG. 14C is an alternate electric-based control implementation wherein a signal pattern comprising a sequence of electrical pulses is simultaneously, periodically applied to the electrodes of the wells of the holding device of FIG. 14A, in accordance with an aspect of the present invention.

FIG. 14A is a simplified schematic of one embodiment of an apparatus, in accordance with an aspect of the present invention. As illustrated, the apparatus includes a current source, such as an AC current source, which is selectively coupled to the active electrodes (1, 2, 3, ... n) in the wells of a holding device, with the electric circuit being completed by the culture medium (not shown) and the illustrated counter electrode. Various pulse sequences may be applied to the electrodes, either sequentially or in parallel. In FIG. 14B, a pulse sequence comprising four pulses is sequentially, periodically applied to the small, active electrodes illustrated in FIG. 14A, while in FIG. 14C, a four-pulse sequence is simultaneously, periodically applied to the small, active electrodes of FIG. 14A.

As noted, the number of pulses in the sequence may vary from one to many, without departing from the concepts of the present invention. The number, amperes and frequency of the applied pulses may be empirically determined for various cell lines and electrode configurations. The goal is to maintain the electrode(s) clear of cell attachment and monolayer growth, while the monolayer is formed over the balance of the well substrate, after which the pulses are discontinued and migration of live cells from the monolayer over the electrode can be monitored.

Those skilled in the art will note from the above description that provided herein are a method and apparatus for performing cell migration analysis, such as an ECIS-based migration assay, for cell lines that are not readily amendable to the previously established electrical wounding technique. Further, the method and apparatus described measure cell migration upon a defined protein layer which has not been changed or modified by the presence of cultured cells over the layer. Additionally, the method and apparatus provided herein allow for a completely automated cell migration assay with little (or no) cell manipulation after inoculation.

One or more aspects of the present invention can be included in an article of manufacture (e.g., one or more computer program products) having, for instance, computer usable media. The media has therein, for instance, computer readable program code means or logic (e.g., instructions, code, commands, etc.) to provide and facilitate the capabilities of the present invention. The article of manufacture can be included as a part of a computer system or sold separately.

One example of an article of manufacture or a computer program product incorporating one or more aspects of the present invention includes, for instance, one or more computer-readable media to store computer readable program code means or logic thereon to provide and facilitate one or more aspects of the present invention. The medium can be an electronic, magnetic, optical, electromagnetic, infrared, or semiconductor system (or apparatus or device) or a propagation medium. Examples of a computer readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

A sequence of program instructions or a logical assembly of one or more interrelated modules defined by one or more computer readable program code means or logic direct the performance of one or more aspects of the present invention.

Although various embodiments are described above, these are only examples.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The capabilities of one or more aspects of the present invention can be implemented in software, firmware, hardware, or some combination thereof At least one program storage device readable by a machine embodying at least one program of instructions executable by the machine to perform the capabilities of the present invention can be provided.

The flow diagram depicted herein is just one example. There may be many variations to this diagram or the steps (or operations) described therein without departing from the spirit of the invention. For instance, certain steps may be performed in a differing order, or steps may be added, deleted, or modified. All of these variations are considered a part of the claimed invention.

Although embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of monitoring cell migration, the method comprising:
   establishing a cell culture within a holding device comprising at least one well for holding the cell culture, the at least one well comprising a well substrate including at least one electrode at least partially exposed to the cell culture, the establishing comprising:
      before cells can attach to the at least one electrode, and before cells can achieve confluence over other portions of the well substrate, periodically applying at least one electrical pulse to the at least one electrode to prevent cells from attaching to the at least one electrode while allowing cells to attach to and achieve confluence over the other portions of the well substrate; and
   discontinuing the periodically applying of the at least one electrical pulse to the at least one electrode, and thereafter, monitoring the cell culture to monitor migration of cells over the at least one electrode from the other portions of the well substrate prior to the cells achieving confluence over the at least one electrode.

2. The method of claim 1, further comprising continuing with the periodically applying of the at least one electrical pulse to the at least one electrode until confluence of cells is achieved over the other portions of the well substrate and at a time thereafter, proceeding with the discontinuing of the periodically applying of the at least one electrical pulse to the at least one electrode, and the monitoring of the cell culture to monitor migration of cells over the at least one electrode.

3. The method of claim 1, wherein the periodically applying comprises periodically applying a sequence of at least two electrical pulses to the at least one electrode to prevent cells from attaching to the at least one electrode while allowing cells to attach to and achieve confluence over the other portions of the well substrate.

4. The method of claim 1, wherein the periodically applying comprises periodically applying an AC electrical signal of at least 1 kHz to the at least one electrode while allowing cells to attach to and achieve confluence over the other portions of the well substrate.

5. The method of claim 1, wherein the monitoring comprises applying an electrical monitoring signal to the at least one electrode after the discontinuing of the periodically applying of the at least one electrical pulse to the at least one electrode, the electrical monitoring signal being a lower current signal than the at least one electrical pulse periodically applied to the at least one electrode to prevent cells from attaching thereto and achieving confluence there over.

6. The method of claim 1, wherein the establishing further comprises initially coating the at least one electrode with a define protein layer, then inoculating the at least one well with cells to establish the cell culture, and wherein the periodically applying prevents inoculated cells from attaching to the at least one electrode, thereby maintaining the define protein layer unaltered over the at least one electrode prior to the discontinuing.

7. The method of claim 1, wherein the at least one well comprises a pair of electrodes, the pair of electrodes comprising an active electrode and a counter electrode, and wherein the monitoring comprises measuring at least one electrical characteristic between the active electrode and the counter electrode of the pair of electrodes in the at least one well.

8. The method of claim 1, wherein the holding device comprises an array of wells for holding cell cultures, each well of the array of wells comprising a well substrate including a pair of electrodes, each pair of electrodes comprising an active electrode and a counter electrode, wherein the well substrate includes at least one opening exposing a portion of the active electrode to the cell culture within the respective well, and wherein the periodically applying comprises sequentially, periodically applying the at least one electrical pulse to the active electrodes of the wells in the array of the holding device.

9. The method of claim 1, wherein the holding device comprises an array of wells for holding cell cultures, each well of the array of wells comprising a well substrate including a pair of electrodes, each pair of electrodes comprising an active electrode and a counter electrode, wherein the active electrode includes at least one opening exposing a portion of the active electrode to the cell culture within the respective well, and wherein the periodically applying comprises simultaneously, periodically applying the at least one electrical pulse to the active electrodes of the wells in the array of the holding device.

10. The method of claim 1, wherein the periodically applying comprises periodically applying a first alternating current (AC) electrical signal to the at least one electrode, the first AC electrical signal having a first frequency and a first current value, and wherein the monitoring comprises applying a second AC electrical signal to the at least one electrode, the second AC electrical signal having a second frequency and a second current value, wherein the second frequency is less than the first frequency, and the second current value is less than the first current value.

11. The method of claim 1, wherein the periodically applying comprises periodically applying a sequence of alternating current (AC) electrical pulses to the at least one electrode to prevent cells from attaching to the at least one electrode while allowing cells to attach to and achieve confluence over the other portions of the well substrate, wherein applying the sequence of AC electrical pulses comprises, at least in part, applying an AC electrical pulse for a first period of time, discontinuing the AC electrical pulse for a second period of time, and then reapplying the AC electrical pulse for the first period of time, and wherein the periodically applying comprises repeating application of the sequence of AC electrical pulses to the at least one electrode for a period of time sufficient to allow cells to attach to and achieve confluence over the other portions of the well substrate.

* * * * *